US012718950B2

(12) United States Patent
Perreault et al.

(10) Patent No.: US 12,718,950 B2
(45) Date of Patent: Aug. 25, 2026

(54) MACHINE LEARNING BASED MEDICAL PROCEDURE ANALYSIS WITH INTERPRETABLE MODEL CONFIDENCE RANKINGS

(71) Applicant: Intuitive Surgical Operations, Inc., Sunnyvale, CA (US)

(72) Inventors: Conor Perreault, Atlanta, GA (US); Aneeq Zia, Lahore (PK)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 18/756,906

(22) Filed: Jun. 27, 2024

(65) Prior Publication Data

US 2025/0006372 A1 Jan. 2, 2025

Related U.S. Application Data

(60) Provisional application No. 63/511,586, filed on Jun. 30, 2023.

(51) Int. Cl.
*G16H 50/20* (2018.01)
*G06V 10/70* (2022.01)
*G06V 20/40* (2022.01)

(52) U.S. Cl.
CPC ............. *G16H 50/20* (2018.01); *G06V 10/70* (2022.01); *G06V 20/41* (2022.01)

(58) Field of Classification Search
CPC ......... G16H 50/20; G06V 10/70; G06V 20/41
See application file for complete search history.

(56) References Cited

U.S. PATENT DOCUMENTS

| | | | | |
|---|---|---|---|---|
| 10,147,052 | B1 * | 12/2018 | Lendvay | G06N 5/022 |
| 2020/0226751 | A1 * | 7/2020 | Jin | A61B 90/37 |
| 2020/0258616 | A1 * | 8/2020 | Likosky | H04N 21/439 |
| 2020/0302600 | A1 * | 9/2020 | Barral | G06V 20/70 |
| 2023/0343079 | A1 * | 10/2023 | Sahni | G06V 10/7788 |
| 2023/0352133 | A1 * | 11/2023 | Chen | G16H 30/20 |

(Continued)

OTHER PUBLICATIONS

Kim MP, Del Calvo H, Chihara R, Chan EY. Video-based curriculum improves resident participation during robot-assisted surgery. J Thorac Dis. Dec. 2022;14(12):4641-4649. doi: 10.21037/jtd-22-603. (Year: 2022).*

(Continued)

*Primary Examiner* — Matthew L Hamilton
(74) *Attorney, Agent, or Firm* — Foley & Lardner LLP

(57) ABSTRACT

The solution for an ML-based medical procedure analysis with interpretable model confidence rankings is disclosed. The solution can include a system having one or more processors, coupled with memory. The system can receive a plurality of input features associated with a prediction for a video stream that captures a procedure performed with a robotic medical system. The prediction can be made via a first model trained with machine learning. The system can determine, via a second model trained with machine learning, a level of confidence in the prediction made via the first model. The system can attribute the level of confidence among at least two input features of the plurality of input features. The system can provide, for display via a display device, an indication overlaid on the video stream of the attribution of the level of confidence among the at least two input features.

20 Claims, 5 Drawing Sheets

(56) References Cited

U.S. PATENT DOCUMENTS

| | | | | |
|---|---|---|---|---|
| 2024/0242818 | A1* | 7/2024 | Venkataraman | G06N 20/00 |
| 2024/0273899 | A1* | 8/2024 | Nallasamy | G06V 10/70 |
| 2025/0148790 | A1* | 5/2025 | Kadkhodamohammadi | G06V 10/454 |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

MACHINE LEARNING BASED MEDICAL PROCEDURE ANALYSIS WITH INTERPRETABLE MODEL CONFIDENCE RANKINGS

CROSS-REFERENCES TO RELATED APPLICATIONS

This application claims the benefit of, and priority to, under 35 U.S.C. § 119, U.S. Provisional Patent Application No. 63/511,586, filed Jun. 30, 2023, which is hereby incorporated by reference herein in its entirety.

BACKGROUND

Medical procedures, such as surgeries, may involve capturing imagery such as video feeds from a variety of viewpoints. For example, in some instances, at least part of surgical procedure may be performed with a computer-assisted robotic medical system. A variety of medical tools may be used in the robotic medical system to perform procedures. Data sources such as cameras and sensors can be used to collect images or data and may be located at various viewpoints in the medical facility to capture and provide imagery of various aspects of the procedure. The captured imagery from the procedure may be processed in various ways.

SUMMARY

The present disclosure is generally directed to machine learning (ML) automated analysis of a medical procedure, such as a surgery, with interpretable model confidence rankings that can mitigate errors caused by the ML-based annotation systems and help inspire more confidence in the ML modeling results. The present solution can include a model trained with machine learning that can annotate a video recording of a medical procedure, such as a surgery, which can be performed using a robotic medical system as well as any range of medical tools. However, challenges in determining a confidence-level or explanation of the confidence-level associated with an accuracy of a particular annotation made via the machine learning model can hinder user confidence in the ML-based annotation solutions.

This technical solution can provide a user with insights into the confidence level determinations with which the ML model makes a prediction without any human intervention and display this information to end users in a way that is interpretable. The technical solution can include a backend system that predicts the model performance on an individual surgical video and provides a user interface that indicates how confident the system is in a prediction made by the model, and the reasons for this confidence.

To predict the model performance, the system can receive input features (e.g., known model performance, model confidence scores, video metadata, video features, objective metric analysis, model output analysis related to workflow and task boundaries, and event stream analysis). The system can use a machine learning model to predict an objective metric of ML quality on a given procedure case, and then leverage sensitivity analysis to attribute the confidence in a ML prediction. For example, the system can determine that 80% of the confidence in a prediction comes from model performance, and 20% of the confidence in the prediction comes from a standard workflow that was predicted. The system can then display the confidence information via a user interface in various ways, including, for example, text, colors, symbols, time stamps, video highlights, etc.

At least one aspect is directed to a system. The system can include one or more processors, coupled with memory. The one or more processors can be configured to receive a plurality of input features associated with a prediction, made via a first model trained with machine learning, for a video stream that captures a procedure performed with a robotic medical system. The one or more processors can be configured to determine, via a second model trained with machine learning, a level of confidence in the prediction made via the first model. The one or more processors can be configured to attribute the level of confidence among at least two input features of the plurality of input features. The one or more processors can be configured to provide, for display via a display device, an indication overlaid on the video stream of the attribution of the level of confidence among the at least two input features.

At least one aspect is directed to a method. The method can include receiving, by one or more processors coupled with memory, a plurality of input features associated with a prediction, made via a first model trained with machine learning, for a video stream that captures a procedure performed with a robotic medical system. The method can include determining, by the one or more processors via a second model trained with machine learning, a level of confidence in the prediction made via the first model. The method can include attributing, by the one or more processors, the level of confidence among at least two input features of the plurality of input features. The method can include providing, by the one or more processors, for display via a display device, an indication overlaid on the video stream of the attribution of the level of confidence among the at least two input features.

At least one aspect is directed to a non-transitory computer readable medium storing program instructions. The program instructions can be for causing at least one processor to receive a plurality of input features associated with a prediction, made via a first model trained with machine learning, for a video stream that captures a procedure performed with a robotic medical system. The program instructions can be for causing at least one processor to determine, via a second model trained with machine learning, a level of confidence in the prediction made via the first model. The program instructions can be for causing at least one processor to attribute the level of confidence among at least two input features of the plurality of input features. The program instructions can be for causing at least one processor to provide, for display via a display device, an indication overlaid on the video stream of the attribution of the level of confidence among the at least two input features.

These and other aspects and implementations are discussed in detail below. The foregoing information and the following detailed description include illustrative examples of various aspects and implementations and provide an overview or framework for understanding the nature and character of the claimed aspects and implementations. The drawings provide illustration and a further understanding of the various aspects and implementations and are incorporated in and constitute a part of this specification. The foregoing information and the following detailed description and drawings include illustrative examples and should not be considered as limiting.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings.

DETAILED DESCRIPTION

Figure 1:
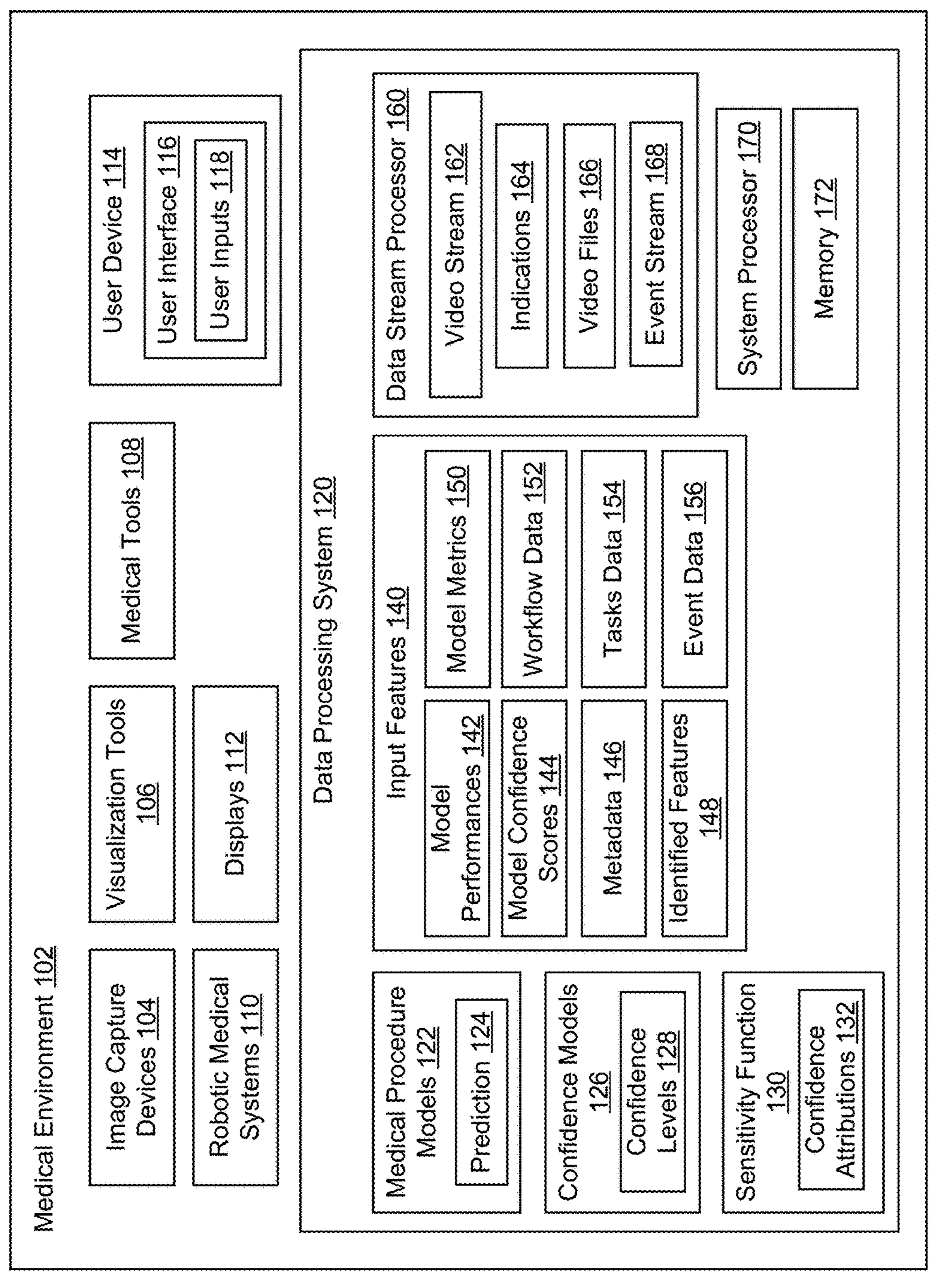
FIG. 1 illustrates an example system for an ML-based medical procedure analysis with interpretable model confidence rankings.

Following below are more detailed descriptions of various concepts related to, and implementations of, methods, apparatuses, and systems of detection of a machine learning based medical procedure analysis with interpretable model confidence rankings. The various concepts introduced above and discussed in greater detail below can be implemented in any of numerous ways.

The present disclosure provides interpretable context for automated ML annotations in medical procedure videos, such as videos of surgical procedures or other medical treatments. The present solution provides annotations of medical treatment surgical video to a user along with an indication of the level of confidence with respect to the prediction made with respect to the ML analysis of the video, as well as the reasons for the particular level of confidence (or lack thereof) allowing for more interpretability around ML-generated annotations.

Data science for medical procedures, such as surgeries, can allow medical professionals (e.g., surgeons) to review their video recorded medical procedures and treatments, refine techniques used in such procedures, and analyze trends across a variety of similar medical procedures or treatments (e.g., across the surgeries or treatments of the same type). For instance, human annotation can be used to provide context and additional metrics around a video recording of a surgery, but ML can improve the scalability of these applications to a commercial level. When ML is used to generate annotations, there can be a risk of making errors that are not caught by a human annotator before being presented to a customer. The present solution provides a way to mitigate any potential errors and inspire more confidence in the ML modeling results by providing some insight into certain portions of the video when the predictions are likely to be correct and descriptions on the portions of the videos when the prediction might be incorrect or contain errors.

This solution can provide systems and methods of commenting or explaining the details and sources of the confidence of model predictions without any human intervention, and displaying this information to the users in a way that is interpretable, allowing the user a greater insight into the model performance. The present solution includes a system that predicts model performance on an individual medical treatment (e.g., surgical) video. This system can use a large set of inputs, such as video metadata, video feature analysis, and analysis of model outputs to predict the accuracy of the ML model(s) that used to analyze the video. The system can implement a sensitivity analysis, depending on the model used, to measure the effect of each input on the output, thereby providing insights (e.g., explanations) to the user indicating the reasons for our confidence or lack of confidence in the prediction. The present solution can include a user interface (UI) that can display the generated insights into model predictions to increase interpretability of ML predictions and trust in the models. The UI can display both an indicator of how confident the system is in a model prediction and the reasons for the given confidence level, allowing the user to understand any potential sources of irregularities in the captured procedure, unusual actions by the surgeon or any potential errors in the predictions.

To provide the desired solution, the system of the present solution can utilize a variety of inputs. The inputs can include a known model performance, which can refer to internal statistics on how well the model performs in specific scenarios based on training and testing datasets. This information can affect the confidence in the model's performance in real-world situations. The inputs can include a model confidence score, which can be generated by one or ML models (e.g., an ensemble ML model) and can provide a measure of certainty in the prediction, allowing for better handling of uncertainty. The inputs can include video metadata, which can include details, such as the type of procedure being analyzed, the hospital site where the data originates, and the robotic system used. The metadata can be compared to the information available during training and testing to assess the similarity between the incoming video and the training data. For instance, if a video is from a new hospital site, there may be less confidence in the model's performance than if the video is from a well-known source. The inputs can include extracted video features, which can be obtained from low-level features or automatic extraction from deep learning models, and which can be used to cluster input videos. Such clustering can provide a higher-level understanding of how a given video compares to the training data. If a video is found to be significantly different from the training data, it can serve as an indication that the model's performance may be compromised or that there is an anomaly in the video recorded procedure. The inputs can include model metrics of model analyses, also referred to as objective metrics analyses, which can include data or metrics from various analyses of surgical videos that can include calculated or extracted objective metrics such as energy used, economy of motion, and achievement of visual milestones. Deviations from the normal distribution of these metrics can signal potential inaccuracies in the ML predictions or anomalies in the procedures.

Analyzing the output of the ML models (or ensemble ML model) can provide further valuable insights. For instance, in case of task recognition and phase recognition, the entire procedure video can be segmented into distinct steps using a single ML model. Comparing segmented workflows to historical, standard or expected workflows can facilitate identifying instances where the model's output differs, indicating a potential error in the model or an anomaly in the procedure. Statistics, such as the duration of a task or an order of the tasks, can act as indicators for predictions that can fall outside of the expected range. The accuracy of the ML models can be cross-checked with system data. By comparing predicted set of tasks to the times when specific tools are used or installed, the system can verify the accuracy of certain tasks that are only feasible using such given tools.

Machine learning models for predicting the quality of a given procedure case can be designed using various techniques. For instance, a first model, which can serve as the foundation for these predictions, can be implemented using different types of statistical or machine learning models, such as linear regression, multilayer perceptron (MLP), or random forest. These models can leverage the input data to make predictions about the objective metric of ML quality associated with a particular procedure case.

In order to provide interpretability to the ML confidence score, sensitivity analysis techniques can be employed. Sensitivity analysis allows for the interpretation of model weights and the assessment of the impact of individual input variables on the model's output. One-at-a-time sensitivity, Sobol indices, and other techniques can be used for this purpose. The specific technique utilized may vary, as there are numerous methods available for sensitivity analysis. However, it is the incorporation of sensitivity analysis that enables the ML confidence score to be interpreted, providing valuable insights into the factors influencing the model's predictions.

By combining machine learning techniques to design the base model and incorporating sensitivity analysis for interpretability, the system gains the ability to predict the objective metric of ML quality for a given procedure case while also providing insights into the factors driving the ML confidence score. This comprehensive approach can enhance the understanding and applicability of the ML models, contributing to improved decision-making and performance assessment in medical procedures.

The present solution can include a user interface that can be used to display outputs from the models to show the amount of confidence in an ML prediction. This can be displayed as a confidence number, or a color indicator to group confidence scores. Outputs from sensitivity analysis can be used to display the effect of each input on the output confidence score. For example a user interface can overlay an indication, such as "80% of the confidence in this prediction comes from model performance, and 20% from a standard workflow that was predicted."

This technology can generate or provide other videos, such as, for example, when a procedure video is flagged as "uncertain" (e.g., including portions of the video recording of a medical procedure in which the confidence level is below a threshold) along with a list of reasons for the uncertainty. For instance, the system can provide a comparison video that is expected or corresponds to a normal or a most common video for a given performance and then give the surgeon more context for why the recorded video of the surgeon's procedure was an outlier. The present system can also point to specific parts of the video that contributed to uncertainty. For example, if there is a specific task/tool combination that was flagged as abnormal, the present solution can jump to this section of the video and let the surgeon directly watch the unusual portion of the video.

The user interface can allow an end user to specify which inputs to consider when making confidence predictions. In some cases, a user may only care about some of the inputs, and the model can receive such selection of inputs and the confidence score can be recalculated, responsive to the input. The present solution can also incorporate feedback from the user, allowing for interaction that can help the end user give feedback with respect to portions of the video recording in which the confidence scores are useful, if the correct predictions are being flagged as inaccurate, and if there are other inputs that should be considered.

FIG. 1 depicts an example system 100, in accordance with some embodiments. The system 100 may be associated with a medical environment 102. Medical environment 102 can include one or more image capture devices 104 for capturing data streams 162 (e.g., videos) of medical procedures or treatments, such as surgeries. Medical environment 102 can include one or more visualization tools 106, medical tools 108, robotic medical systems 110 and displays 112. Medical environment 102 can include a user device (e.g., a computer station) with a user interface 116 to receive user inputs 118, such as comments from a medical professional in response to prompts for comments on particular portions of data (e.g., video) stream of a recorded medical procedure. Medical environment 102 can further include a data processing system 120. Data processing system 120 can include one or more medical procedure models 122 providing predictions 124, one or more confidence models 128 providing confidence levels 128 with respect to the predictions 124 and one or more sensitivity functions 130 for providing confidence attributions 132 (e.g., apportionment of the reasons for the given confidence level 128 to individual input features 140). Data processing system 120 can include one or more input features 140, data stream processors 160, system processors 170 and memories 127. Input features 140 can include one or more model performances 142, model confidence scores 144, metadata 146, identified features 148, model metrics 150, workflow data 154, tasks data 154 and event data 156. Data stream processors 160 can include one or more video streams 162, indications 164, video files 166 and event streams 168.

Medical environment 102 can include any medical environment, such as a surgical environment, operating rooms, intensive care units, radiology laboratories, pathology laboratories, rehabilitation centers, recovery units, emergency departments, mental health facilities or any other medical environment in which a medical procedure or a treatment can be provided to patients. A medical environment, corresponding to a surgical environment, can include a surgical facility such as an operating room in which a surgical procedure, whether, invasive, non-invasive, in-patient, or out-patient, may be performed on a patient. System 100 can be associated with different types of medical sessions or activities, or non-medical environments that may require removal of non-surgical information from a data stream captured from that environment.

System 100 can include one or more image capture devices 104, such as one, two, five, 10 or more image capture devices 104, each of which can have their output data streams 162 (e.g., images, video and/or audio) received, processed, or managed by a data stream processor 160 of the data processing system 120. Each of the image capture devices 104 can be configured to capture images from a particular viewpoint within the medical environment 102. Thus, each of the image capture devices 104 can be positioned, mounted, or otherwise located based on content that is desired to be captured from a particular viewpoint. For example, at least one of the image capture devices 104 can be positioned to capture one or more images of an area where a patient is located within the medical environment 102. An image capture devices 104 can be positioned to capture one or more images of an area where one or more medical professionals are located within the medical environment 102. An image capture devices 104 can be configured to capture one or more images of other designated areas within the medical environment 102. The image capture devices 104 can include any of a variety of sensors, cameras, video imaging devices, infrared imaging devices, visible light imaging devices, intensity imaging devices (e.g., black, color, grayscale imaging devices, etc.), depth imaging devices (e.g., stereoscopic imaging devices, time-of-flight imaging devices, etc.), medical imaging devices such as endoscopic imaging devices, ultrasound imaging devices, etc., non-visible light imaging devices, any combination or sub-combination of the above mentioned imaging devices, or any other type of imaging devices that can be suitable for the purposes described herein.

Video stream 162 that is captured by the image capture devices can include images, such as still images, video images (e.g., video frames), vector images, bitmap images, other types of images, or combinations thereof. One or more of the image capture devices 104 can be configured to capture other parameters such as sound, motion, pressure, temperature, etc. within the medical environment 102 as well. The image capture devices 104 can capture the images at any suitable predetermined capture rate and/or frequency. Other settings, such as zoom settings, etc. of each of the image capture devices 104 can vary as desired to capture suitable images from a particular viewpoint. In some embodiments, one or more of the image capture devices 104 can have fixed locations, positions, and/or orientations. In other embodiments, one or more of the image capture devices 104 can be portable, or otherwise configured to change orientation or telescope in various directions. In some embodiments, one or more of the image capture devices 104 can be part of a multi-sensor architecture including multiple sensors, with each sensor being configured to detect, measure, or otherwise capture a particular parameter (e.g., sound, images, pressure, etc.).

The images captured by the image capture devices 104 can be sent as data stream components to a visualization tool 106. A data stream component can be considered any sequence of digital encoded data or analog data (e.g., video frames, audio data, images, sensor readings, etc.) from a data source such as the image capture devices 104. The visualization tool 106 can be configured to receive a plurality of data stream components and combine the plurality of data stream components into a single data stream (e.g., video stream 162). In some embodiments, the visualization tool 106 can be configured to receive up to five or more different data stream components (e.g., one from each image capture device). In addition to receiving the data stream components from the image capture devices 104, the visualization tool 106 can also receive a data stream component from a medical tool 108. The medical tool 108 can be any type and form of tool used for surgery, medical procedures or a tool in an operating room or environment associated with or having an image capture device. In some embodiments, the medical tool 108 can be an endoscope for visualizing organs, tissues, etc. within a body of the patient. In some embodiments, the medical tool 108 can include other or additional types of therapeutic and/or diagnostic medical imaging implements. The medical tool 108 can be configured to be installed in a robotic medical system 110.

The robotic medical system 110 can be a computer-assisted system configured to perform a surgical or medical procedure or activity on a patient via or using or with the assistance of one or more robotic components and/or medical tools. As described in more detail below, the robotic medical system 110 can include one or more manipulator arms that perform one or more computer-assisted medical tasks. The medical tool 108 can be installed on a manipulator arm of the robotic medical system 110 to perform a surgical task. In such instances, images (e.g., video images) captured by the medical tool 108 can be sent to the visualization tool 106. The robotic medical system 110 can also include one or more input ports to receive direct or indirect connection of one or more auxiliary devices. For example, in some embodiments, the visualization tool 106 can be connected to the robotic medical system 110 to receive the images from the medical tool when the medical tool is installed in the robotic medical system (e.g., on a manipulator arm of the robotic medical system). The visualization tool 106 can combine the data stream components from the image capture devices 104 and the medical tool 108 into a single combined data stream for presenting on a display 112. In some embodiments, the display 112 can be associated with a user control system or other type of display system, whether within the medical environment 102 or remote, to view the single combined data stream.

The system 100 also includes a data processing system 120 associated with the medical environment 102. The data processing system 120 can include a data stream processor 160 configured to access the single combined data stream from the visualization tool 106 and/or the display 112. The single combined data stream received by the data stream processor 160 can be referred to as a data stream 162 or a video stream 162. Data or video stream 162 can include a captured medical procedure (e.g., surgery) as viewed from one or more sources (e.g., image capture devices 104 and/or medical tools 108). Video stream 162 can include a series of image frames from a variety of angles or vintage points with respect to the procedure activity (e.g., point or area of surgery), as well as any sound data, temperature data, pressure data, patient's vital signs data or any other data corresponding to the procedure).

The data stream processor 160 can be configured to receive an event stream 168 from the robotic medical system 110. The event stream 168 can include a stream of event data or information, such as packets, that identify or convey a state of the robotic medical system 110 or an event that occurred in association with the robotic medical system or surgical or medical surgery being performed with the robotic medical system. An example state of the robotic medical system 110 can indicate whether the medical tool 108 is installed on a manipulator arm of the robotic medical system or not, whether it was calibrated, or whether it was fully functional (e.g., without errors) during the procedure. For example, when the medical tool 108 is installed on a manipulator arm of the robotic medical system 110, a signal or data packet(s) can be generated indicating that the medical tool has been installed on the manipulator arm of the robotic medical system 110. The signal or data packet(s) can be sent to the data stream processor 160 as the event stream 168. Another example state of the robotic medical system 110 can indicate whether the visualization tool 106 is connected, whether directly to the robotic medical system or indirectly through another auxiliary system that is connected to the robotic medical system.

Similar to the medical tool 108, when the visualization tool 106 is directly plugged into the robotic medical system 110 or plugged into another auxiliary system that is plugged into a port of the robotic medical system, the robotic medical system 110 can generate a signal or data packet(s) that can be sent to the data stream processor 160 as the event stream 168. Yet another state of the robotic medical system 110 can indicate whether another auxiliary system is connected to (e.g., plugged into) any of the ports of the robotic medical system. The robotic medical system 110 can have other states, which can be detected by the data stream processor 160. In some embodiments, the data stream processor 160 can be configured to determine (e.g., record) or otherwise receive the event stream 168 through an Application Programming Interface (API) of the robotic medical system 110. In other embodiments, the data stream processor 160 can determine or otherwise receive the event stream 168 via other suitable mechanisms. In some embodiments, the data stream processor 160 can poll the robotic medical system 110 to determine the state of the robotic medical system.

The data stream processor 160 can receive the data stream 162 and the event stream 168. Based on the data stream 162 and the event stream 168, the data stream processor 160 detects if the data stream includes any non-surgical information (e.g., PHI). In some embodiments, the non-surgical information can include, in addition to that described above, any out-of-body information of the patient, including for example, any features or identifiers that can be indicative of an identity of the patient or any features that depict, or can be visible from, an exterior of the body of a patient in a non-surgical state. In contrast, in-body information can be indicative of an interior of the body of the patient and may not be considered non-surgical information.

Data stream processor 160 can generate indications 164 that can include or reflect the predictions 124 and/or confidence levels 128. Indications 164 can include insights, annotations or comments on various tasks, actions or portions of the procedure captured on the video stream 162. Indications 164 can include any combination of any one or more of: predictions 124, confidence levels 128 or confidence attributions with respect to particular input features 140. For example, indications 164 can include comments or descriptions of various tasks performed during a portion of a surgery. The comments or descriptions can be generated according to, or based on, predictions 124 for that particular task. The comments or descriptions reflecting the predictions 124 can include confidence levels 128 as well as confidence attributions 132 for the given confidence levels 128 with respect to input features 140.

The data processing system 120 can use the generated confidence score to support various annotation functions, or displayed via a front end (e.g., user interface 116). The confidence score can be used to support human in the loop annotation by either only providing to via the user interface an indication of annotations with a confidence score that satisfies a threshold, or displaying multiple possible annotations with respective threshold scores. Thus, a user can more efficiently select an annotation using the confidence score information. Further, the data processing system 120 can improve performance of model retraining by providing corrected annotations or confidence scores on the user interface 116 that can be used as improved training data or input to a model.

Data stream processor 160 can generate video files 166 according to particular portions of the video stream 162 of the procedure that falls above or below a particular confidence level threshold 128. For example, portions of the video stream 162 for which confidence level 128 for the prediction 124 is below a threshold level (e.g., below 90%, 85%, 80%, 75%, 70% or less) can be gathered and organized to form a video file 166. Such a video file 166 can be provided, via a user interface 116 to a user (e.g., a surgeon) to request the user to provide comments or explanations for the given portions of the video file 166 for which the confidence levels 128 are below the threshold. The user (e.g., surgeon) can provide the comments or explanations via user inputs 118, which the medical procedure model 122 and/or confidence model 126 can include into their input features 140 and use to update the confidence levels 128, as well as for future predictions 124, confidence level 128 determinations, and/or confidence attributions 132.

Modification of the data stream 162 can include blurring non-surgical information, redacting or blocking non-surgical information, deleting or removing non-surgical information, overwriting non-surgical information, or otherwise scrubbing out the non-surgical information using other ways. The data stream processor 160, also referred to as the data stream modification processor 160, can store the data stream 162 that has been modified. A database in a memory 172 can include, or be associated with, a local storage attached to the data stream processor 160 and/or the data processing system 120, a network attached storage such as a cloud storage associated with the recording device and/or the data processing system, or a combination of a local attached storage and a network attached storage. The database can store the data stream 162, with and/or without modification to allow later retrieval, access, viewing, and/or processing of the data stream.

In some embodiments, the data stream processor 160 can highlight, identify, and/or annotate portions of the data stream 162. For example, in some embodiments, the data stream processor 160 can highlight the portions of the data stream 162 that are received from the medical tool 108 when installed in the robotic medical system 110. In some embodiments, the data stream processor 160 can add a notation or indication in real-time on the data stream 162 on portions of the data stream 162 that are from the medical tool 108 and/or from the image capture devices 104. In some embodiments, the data stream processor 160 can also be configured to send alerts, for example, when the event stream determines that the medical tool 108 is installed in the robotic medical system 110, when the visualization tool 106 is connected to the robotic medical system, when the data stream is modified, etc.

Input features 140 can include any type and form of inputs into a confidence model 126 or a sensitivity function 130. Input features 140 can include outputs from the medical procedure model 122. Input feature 140 can include a model performances 142 information or data, model confidence scores 144, metadata 146, identified features 148 from the video stream 162, model metrics 150, workflow data 152, tasks data 154 and event data 156. Input features 140 can vary throughout the video stream 162 depending on the contents of the video stream 162 within various portions. Input features 140 can be used as inputs in determining confidence levels 128 and/or confidence attributions 132 and can vary in impact on the confidence levels 128 and/or confidence attributions or apportionment based on contextual information or determinations by the models 122 and/or 126.

Model performances 142, also referred as the known model performance 142, can include internal statistics on how well the model performs in specific scenarios based on training and testing datasets. This information can affect or influence the confidence levels 128 in the captured procedure (e.g., surgery or medical treatment) in view of other performances in real-world situations that were used to train the medical procedure model 122. By considering the known model performance 142 (e.g., comparison of the procedure captured in the video stream 162 against the trained model performances 142), model procedure model 122 can make predictions 124 with respect to the captured procedure with a greater degree of confidence level 128, and therefore more reliably and accurately make the predictions 124.

Model confidence score 144 can include any scores corresponding to the captured procedure (e.g., surgery captured in the video stream 162) with respect to other similar procedures (e.g., surgeries of the same type) on which the medical procedure 122 can be trained. Model confidence score 144 can compare the various tasks data 154, workflow 152, event data 154 or other input features 140 to determine the score that can be used to provide or indicate a measure of confidence level 128 in the predictions 124. Model confidence score 144 can allow for improved handling of uncertainty and helps in decision-making processes. By incorporating the model confidence score 144, the system can make more informed judgments based on the level of confidence associated with each prediction 124.

Metadata 146 can include any data or information on the video stream 162, such as the type of a video stream 162, its origin, authors, medical professionals involved, or any other data. Metadata 146 can include details such as the type of procedure being captured or analyzed, the hospital site where the video data originates, and the robotic system used. Metadata 146 can include information on the medical professionals (e.g., doctors performing the surgery), tools used in the procedure and/or type of image capture devices 104 or medical tools 108 used to acquire the video stream 162. By comparing this metadata 146 to the information available during training and testing, the system can assess the similarity between the incoming video and the training data. For instance, if the video is from a new hospital site, there may be less confidence in the model's performance compared to a video from a well-known source. Metadata 146 can help contextualize the video stream 162 captured and adjust the expectations in the models 122 and 126, accordingly.

Identified features 148 can include any information or data on features, items, objects or persons identified in the video stream 162. Identified features 148 can include specific medical tools 108 identified in the video stream 162 at specific portions of the video stream 162, specific events (e.g., from event stream 168), specific parts of a body (e.g., doctor's fingers, arms or hands, as well as patient's body parts on which a surgery is performed). Identified features 148 can include extracted video features that can serve as valuable input features 140 for the confidence model 126 and/or sensitivity function 130. Identified features 148 can be obtained from low-level features or automatic extraction from deep learning models. These features are used to cluster input videos, providing a higher-level understanding of how a given video compares to the training data. If a video stream 162 varies significantly (e.g., by more than a predetermined threshold amount) from the training data (e.g., surgical procedures of the same type as the one captured in the video stream 162), concerns can be raised about the model's performance (e.g., affecting the confidence level 128) or indicating anomalies in the recorded procedure in the video stream 162. Identified features 148 can therefore help identify unusual or out-of-distribution cases that can trigger further examination, such as by prompting user inputs 118 to the user (e.g., a surgeon) to allow the surgeon to comment on the likely reasons for the identified anomalies.

Model metrics 150, also referred to as the objective metrics analysis 150, can include various analyses of surgical videos, calculating or extracting objective metrics such as energy used, economy of motion, and achievement of visual milestones. Model metrics 150 can include deviations from the normal distribution of various tasks, actions or motions in the procedures used in the training of the medical procedure model 122. Model metrics 150 can indicate potential inaccuracies in the ML predictions 124 or anomalies in the procedures captured in the video stream 162. By considering model metrics 150, the system can gain insights into the quality and effectiveness of the surgical procedures, contributing to more reliable predictions and assessments.

Workflow data 152 can include any data or information on an order of tasks or actions in the procedure captured by the video stream 162. Workflow data 152 can be used in task recognition and phase recognition in order to identify and detect certain tasks and/or phases of the procedure, such as the exposure, dissection, transaction, reconstruction and/or extraction. For example, the entire procedure video stream 152 can be segmented into distinct steps using a medical procedure model 122. By comparing segmented steps of the workflow to known model performances 142 (e.g., of workflows of known procedures of the same type), various instances where the model's output differs from the captured procedure can be identified, indicating potential errors or deviations from the expected workflow or order of tasks. Simple statistics such as the duration of a particular task or the order of tasks can also serve as indicators for predictions that fall outside the expected range. Analysis of workflow data 152 can provide valuable insights into the accuracy and consistency of the ML models, aiding in the identification of anomalies and the improvement of overall performance, as well as the establishment of the confidence levels 128 in the given predictions 124.

Tasks data 154 can include any data or information on individual tasks or steps in the procedure captured by the video stream 162. Tasks data 154 can allows for cross-checking of the accuracy of the ML models using system data. By comparing the predicted set of tasks from the workflow data 152 in comparison with the model performances 142, tasks data 154 can be used to determine a confidence level 128 in a prediction 124 that particular task is performed. By comparing the predicted set of tasks to the times when specific medical tools 108 are used (e.g., from identified features 148) or installed (e.g., from event data 154), data processing system 120 can verify the accuracy of whether the given tasks were performed as they can be feasible only with particular medical tools 108. Tasks data 154 can provide a way to validate the predictions 124 made by the medical procedure model 122 by aligning tasks data 154 with the actual utilization of medical tools 108 during the procedure, thereby checking the use of tools aligns with the trained models in order to determine the confidence levels 128. By leveraging tasks data 154, data processing system can gain confidence in the accuracy of the predictions and ensures the models 122 and 126 are effectively capturing the dependencies and requirements associated with specific tasks.

Event data 156 can include any information on specific events that can be used to verify particular modeled inferences or facts. For example, an event data 156 can include information on when a particular medical tool 108 was installed for the purposes of a recorded procedure. For example, if a medical tool 108 was not present in the given facility in which the procedure was performed at the time of the procedure, the confidence level 128 can be reduced. Event data 156 can include information about the date of calibration of any medical tool 108, time of day the procedure was performed, year or month in which was performed or any other temporal information. Event data 156 can include information about whether procedure was performed at a different emergency location, such as a natural disaster zone or an area in which many patients were injured in a short amount of time. Event data 156 can be used to double check or verify any of the input features 140 and adjust the confidence level with respect to predictor 124 accordingly. Event data 156 can include events from data or video stream, such as kinetics (e.g., motion or movement recognition, such as movement of a surgeon), events captured via image capture devices 104 or medical tools 108, such as energy use, firefly use (e.g., change in visual) and camera clutch.

Data processing system 120 can include one or more machine learning models, such as the medical procedure models 122 and confidence models 126. These machine learning models can include or be coupled with sensitivity functions 130 to determine and assign confidence attributions to various input features 140. Medical procedure models 122 and/or confidence models 126 can include, employ or utilize any machine learning techniques suitable for performing the functions described herein. For instance, medical procedure models 122 and confidence models 126 can be, include or utilize any deep learning neural network or other computer-vision model trained to receive the data steam 162 as an input and determine predictions confidence levels 128 for the predictions 124. In some embodiments, medical procedure model 122 and confidence model 126 are combined into a single model, either separate from or combined with (e.g., including), a sensitivity function 130.

Models 122 and 126 can be developed including or using a variety of machine learning models and techniques. These models can include linear regression, which can captures linear relationships between input features 140 and the target variables. These models can include multilayer perceptron (MLP), a neural network model capable of handling complex non-linear relationships, and random forest, an ensemble of decision trees that considers multiple decision paths. These models can utilize input data such as video recordings and procedural characteristics to make predictions about the objective metric of ML quality. In surgical procedures, for example, the models 122 and/or 126 can analyze or consider factors like procedure duration, precision of surgical movements, and achievement of milestones. By training the model on a dataset with input features and corresponding objective metric values, it can learn the patterns and relationships to make predictions 124 for new cases (e.g., procedures captured in the videos stream 162).

The model 122 can refer to or include an ensemble model. The model 126 can refer to or include an ensemble model. One or both of models 122 and 126 can form an ensemble model or a part of an ensemble model. An ensemble model can refer to or include a type of machine learning model that combines predictions from multiple individual models to provide a more accurate and reliable prediction than a single model may achieve. The ensemble model can leverage the strengths and mitigate weaknesses of different models by combining them. For example, to combine multiple models, the ensemble model can employ a random forest that includes an ensemble of decision trees, boosting via sequentially trained models, stacking via multiple base models that become input features to a meta-learner, voting, or blending. Thus, the data processing system 120 can generate the confidence score using an ensemble model.

Medical procedure model 122 can identify specific frames or locations of the data stream 162 that include, identify or relate to specific input features 140, including, for example, identified features 148 (e.g., medical tools 108 or robotic medical systems 110), model metrics 150, workflow data 152, tasks data 154 and events data 156. The medical procedure model 122 can be configured to detect, classify, and/or categorize specific types of the events or tasks in the procedure, determine the workflow of the procedure (e.g., surgery) into a series and/or arrangement of tasks and/or actions. For example, the medical procedure model 122 can identify all of the tasks or actions in a particular surgery procedure and identify the prediction 124 as to whether the procedure tasks were performed in accordance with the modeled procedures corresponding to the captured or recorded procedure from the video stream 162. Medical procedure model 122 can receive as its input the video stream 162 of the medical procedure (e.g., surgery) performed and provide as its output input features 140.

Inputs to the confidence model 126 can include information about agreement between multiple predictive models. Agreement can refer to or include whether outputs from the multiple predictive models are similar with one another, match one another, consistent with one another, in alignment with one another, linked with one another, grouped with one another, associated with one another, or are not contradictory. For example, if the outputs from multiple predictive models can be in agreement if they are outputs for a same value and the values are within a threshold of one another or a percentage threshold of one another, such as +/−10%, for example. Outputs of predictive models can be in agreement with one another if the predicted outputs are consistent with one another. For example, if a phase model predicts that the medical procedure in a first type of phase, and a step model predicts that the step is a first type of step, then the outputs can be in agreement if it is predetermined or there is a priori knowledge that indicates that the first type of step occurs or is likely to occur during the first type of phase. If, however, the first type of step does not occur or rarely occurs during the first type of phase, then the data processing system can determine that the two models are not in agreement with one another or lack agreement. The multiple predictive models can include, for example, a phase model, step model, a medical procedure model, or other types of models.

The data processing system 120 can provide an indication of whether the models are in agreement with another. The indication can be a binary indication of agreement (e.g., yes/no, 0/1, agreed/disagree), or provide a level or degree of agreement. The level or degree of agreement can be a numerical score or a letter or grade, for example. The numerical score or level of agreement can have a range or scale, such as 0 to 1, 0 to 10, 0 to 100, or some other range or scale, with either the smallest number or largest number representing the greatest or least amount of agreement. The indication of the level of agreement can have a letter grade, such as A, B, C, D or F, or other indication such as low, medium or high.

The indication of the level of agreement can identify the models whose outputs are being compared along with a quantification of the level of agreement. The indication of the level of agreement can be used to generate a confidence score. For example, the indication of the level of agreement between multiple models or ensemble models can be input into the confidence model 126 to generate the confidence score.

The confidence model 126 can include any deep learning neural network or computer-vision model trained to receive the input features 140 and provide a confidence level 128 with respect to any prediction 124. The confidence level 128 can vary with respect to any one or more predictions 124 according to any data, information or inferences made by the confidence models and/or sensitivity functions 130 with respect to any input features 140. Confidence model 126 can include the functionality (e.g., sensitivity function 130) for determining attribution (e.g., apportionment or portions) of the confidence level 128 for each of the input features 140 that can be input into the confidence model 126. Confidence model 126 can include the functionality for identifying portions of the video stream 162 corresponding to various degrees of confidence levels 128. For example, confidence model 126 can be configured to identify portions of the video stream 162 for which the confidence level 128 in the corresponding prediction 124 for those portions of the video stream 162 are below a particular threshold level. The threshold level can be a predetermined threshold level, or it can be a percentage level with respect to other confidence levels 128 in the video stream 162, such as for instance the lowest percentage level (e.g., lowest quartal or lowest 25% of confidence level 128 values or below) for all the confidence levels 128 throughout the video stream 162.

Sensitivity function 130 can include any statistical tool or a function that quantifies the relationship between changes in input features 140 and the resulting changes in the output or response variables of a model. Sensitivity function 130 can be included in a confidence model 126. Sensitivity function 126 can determine how sensitive predictions 124 are to variations in the input features 140. Sensitivity function 130 can utilize or include a shortest path determination, which can compute the shortest path to highest confidence in terms of modeled input features 140. Sensitivity function 130 can identify the combination of input features 140 that maximizes the confidence score or level of uncertainty in the model's predictions and use that technique to identify the confidence levels or attributions 132 for each input feature 140. Sensitivity function 130 can include the functionality to identify which input features 140 have the most significant impact on the confidence model 126 output and the extent to which changes in those variables influence the resulting confidence levels 128. Sensitivity function 130 can include a variety of forms, such as interpretation of model weights, one-at-a-time sensitivity analysis, Sobol indices, or other sensitivity analysis techniques. Sensitivity function 130 can include a quantitative measure of the sensitivity and importance of one or more input features 140 in relation to the prediction 124 and/or confidence levels 128, as well as identify confidence attributions (e.g., portions of confidence level 128 for each individual input feature 140).

Although shown as separate machine learning models, in some embodiments, the non-medical procedure model 122 and confidence model 126, as well as the sensitivity function 130, can be configured as any combination of two models or functions, or as a single machine learning model performing all of the combined functions of these three components. Further, although shown separate from the data stream processor 160, in some embodiments, the machine learning models 122 and 126 can be a part of the data stream processor 160. In some embodiments, the machine learning models 122 and 126 can be located in a remote location (e.g., a cloud or a server farm) and can be accessible to the data stream processor 160 over a network (e.g., internet).

Prediction 124 can include any determination by a medical procedure model 122 with respect to a procedure captured by a data or video stream 162. Prediction 124 can include an insight, a comment or an explanation of a task, an action or a portion of a procedure captured in the video stream 162 that can be determined by a medical procedure model 122 based on the images, sounds or data in the video stream 162 compared against a modeled procedure learned or trained based on various data from any number of medical procedures. For example, a prediction 124 can include a determination of a type of procedure performed, a particular phase of the procedure being undertaken, a particular task within the procedure being implemented, a particular type of medical tool 108 being used, or any other information, commentary, insight or conclusion on the procedure shown in the video stream 162.

Confidence levels 128 can include any determination of a level of confidence with which the prediction 124 is determined. For example, confidence level 128 can include a level of confidence of, for example, 90% to 95% that a particular prediction 124 is correct, or a level confidence 128 of about 72% that a prediction 124 that a particular task is complete in the procedure. Confidence levels 128 can be determined based on any changes in input features 140 or any inferences or analysis of input features 140 with respect to modeled procedure in the models 122 and/or 126.

Confidence attributions 132 can include an apportionment or a portion of the confidence level 128 with respect to any given input feature 140. For example, some input features 140 can influence a confidence level 128 to fall below a particular threshold level (e.g., below 80%). In such an example, that particular input feature 140 can be identified as the leading cause for that particular confidence level 128 for a given prediction 124. For example, the particular input feature 140 can be assigned an attribution or a portion of confidence level 128 of about 70%, indicating that this given input feature 140 is 70% responsible for that confidence level 128 value or score. Confidence attributions 132 can be assigned to a plurality of input features 140, depending on the sensitivity function 130 determining how such input features 140 influence the confidence levels 128 for the given prediction 124.

The data processing system 120, the data stream processor 160, and/or components thereof can include a physical or virtual computer system operatively coupled, or associated with, the medical environment 102. In some embodiments, the data processing system 120, the data stream processor 160, and/or components thereof can be coupled, or associated with, the medical environment 102 via a network, either directly or directly through an intermediate computing device or system. The network can be any type or form of network. The geographical scope of the network can vary widely and can include a body area network (BAN), a personal area network (PAN), a local-area network (LAN) (e.g., Intranet), a metropolitan area network (MAN), a wide area network (WAN), or the Internet. The topology of the network can assume any form such as point-to-point, bus, star, ring, mesh, tree, etc. The network can utilize different techniques and layers or stacks of protocols, including, for example, the Ethernet protocol, the internet protocol suite (TCP/IP), the ATM (Asynchronous Transfer Mode) technique, the SONET (Synchronous Optical Networking) protocol, the SDH (Synchronous Digital Hierarchy) protocol, etc. The TCP/IP internet protocol suite can include application layer, transport layer, internet layer (including, e.g., IPv6), or the link layer. The network can be a type of a broadcast network, a telecommunications network, a data communication network, a computer network, a Bluetooth network, or other types of wired and wireless networks.

The data processing system 120, the data stream processor 160, and/or components thereof, can be located at least partially at the location of the surgical facility associated with the medical environment 102 or remotely therefrom. At least some elements of the data processing system 120, the data stream processor 160, and/or components thereof can be accessible via portable devices such as laptops, mobile devices, wearable smart devices, etc. The data processing system 120, the data stream processor 160, and/or components thereof can include other or additional elements that can be considered desirable to have in performing the functions described herein. The data processing system 120, the data stream processor 160, and/or components thereof, can include, or be associated with, a system processor 170.

The system processor 170 can execute one or more instructions associated with the system 100. The system processor 170 can include an electronic processor, an integrated circuit, or the like including one or more of digital logic, analog logic, digital sensors, analog sensors, communication buses, volatile memory, nonvolatile memory, and the like. System processor 170 can be, or can include, processor 410. The system processor 170 can include, but is not limited to, at least one microcontroller unit (MCU), microprocessor unit (MPU), central processing unit (CPU), graphics processing unit (GPU), physics processing unit (PPU), embedded controller (EC), or the like. The system processor 170 can include, or be associated with, a memory 172 operable to store or storing one or more non-transitory computer-readable instructions for operating components of the system processor and operating components operably coupled to the system processor. The one or more instructions can include at least one of firmware, software, hardware, operating systems, embedded operating systems, and the like. The system processor 170 or the system 100 generally can include at least one communication bus controller to effect communication between the system processor and the other elements of the system 100.

The memory 172 can include one or more hardware memory devices to store binary data, digital data, or the like. Memory 172 can be, or can include, main memory 415 and/or storage device 425. The memory 172 can include one or more electrical components, electronic components, programmable electronic components, reprogrammable electronic components, integrated circuits, semiconductor devices, flip flops, arithmetic units, or the like. The memory 172 can include at least one of a non-volatile memory device, a solid-state memory device, a flash memory device, a NAND memory device, a volatile memory device, etc. The memory 172 can include one or more addressable memory regions disposed on one or more physical memory arrays.

Figure 2:
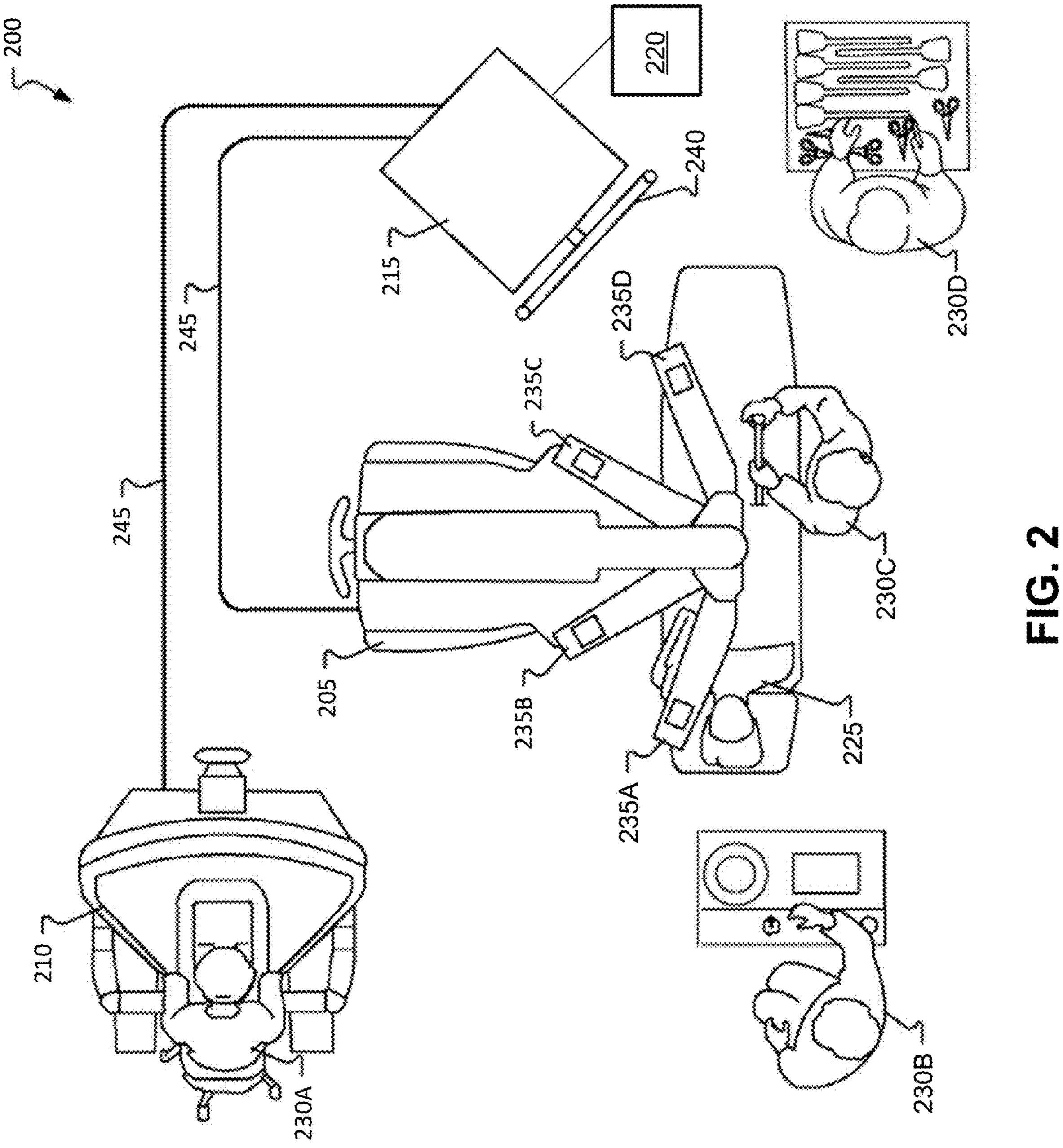
FIG. 2 illustrates a block diagram showing an example medical procedure environment, such as a surgical environment, in accordance with the embodiments of the present solution.

Referring to FIG. 2, a surgical system 200 is shown, in accordance with some embodiments. The surgical system 200 can be an example of the medical environment 102. The surgical system 200 can include a robotic medical system 205 (e.g., the robotic medical system 110), a user control system 210, and an auxiliary system 215 communicatively coupled one to another. A visualization tool 220 (e.g., the visualization tool 106) can be connected to the auxiliary system 215, which in turn can be connected to the robotic medical system 205 (e.g., robotic medical system 110). Thus, when the visualization tool 220 is connected to the auxiliary system 215 and this auxiliary system is connected to the robotic medical system 205, the visualization tool can be considered connected to the robotic medical system. In some embodiments, the visualization tool 220 can additionally or alternatively be directly connected to the robotic medical system 205.

The surgical system 200 can be used to perform a computer-assisted medical procedure on a patient 225. In some embodiments, surgical team can include a medical professional (e.g., surgeon, or any other doctor or medical treatment providing professional) 230A and additional medical personnel 230B-230D such as a medical assistant, nurse, and anesthesiologist, and other suitable team members who can assist with the surgical procedure or medical session. The medical session can include the surgical procedure being performed on the patient 225, as well as any pre-operative (e.g., which can include setup of the surgical system 200, including preparation of the patient 225 for the procedure), and post-operative (e.g., which can include clean up or post care of the patient), and/or other processes during the medical session. Although described in the context of a surgical procedure, the surgical system 200 can be implemented in a non-surgical procedure, or other types of medical procedures or diagnostics that can benefit from the accuracy and convenience of the surgical system.

The robotic medical system 205 can include a plurality of manipulator arms 235A-235D to which a plurality of medical tools (e.g., the medical tool 108) can be coupled or installed. Each medical tool can be any suitable surgical tool (e.g., a tool having tissue-interaction functions), imaging device (e.g., an endoscope, an ultrasound tool, etc.), sensing instrument (e.g., a force-sensing surgical instrument), diagnostic instrument, or other suitable instrument that can be used for a computer-assisted surgical procedure on the patient 225 (e.g., by being at least partially inserted into the patient and manipulated to perform a computer-assisted surgical procedure on the patient). Although the robotic medical system 205 is shown as including four manipulator arms (e.g., the manipulator arms 235A-235D), in other embodiments, the robotic medical system can include greater than or fewer than four manipulator arms. Further, not all manipulator arms can have a medical tool installed thereto at all times of the medical session. Moreover, in some embodiments, a medical tool installed on a manipulator arm can be replaced with another medical tool as suitable.

One or more of the manipulator arms 235A-235D and/or the medical tools attached to manipulator arms can include one or more displacement transducers, orientational sensors, positional sensors, and/or other types of sensors and devices to measure parameters and/or generate kinematics information. One or more components of the surgical system 200 can be configured to use the measured parameters and/or the kinematics information to track (e.g., determine poses of) and/or control the medical tools, as well as anything connected to the medical tools and/or the manipulator arms 235A-235D.

The user control system 210 can be used by the surgeon 230A to control (e.g., move) one or more of the manipulator arms 235A-235D and/or the medical tools connected to the manipulator arms. To facilitate control of the manipulator arms 235A-235D and track progression of the medical session, the user control system 210 can include a display (e.g., the display 112) that can provide the surgeon 230A with imagery (e.g., high-definition 3D imagery) of a surgical site associated with the patient 225 as captured by a medical tool (e.g., the medical tool 108, which can be an endoscope) installed to one of the manipulator arms 235A-235D. The user control system 210 can include a stereo viewer having two or more displays where stereoscopic images of a surgical site associated with the patient 225 and generated by a stereoscopic imaging system can be viewed by the surgeon 230A. In some embodiments, the user control system 210 can also receive images from the auxiliary system 215 and the visualization tool 220.

The surgeon 230A can use the imagery displayed by the user control system 210 to perform one or more procedures with one or more medical tools attached to the manipulator arms 235A-235D. To facilitate control of the manipulator arms 235A-235D and/or the medical tools installed thereto, the user control system 210 can include a set of controls. These controls can be manipulated by the surgeon 230A to control movement of the manipulator arms 235A-235D and/or the medical tools installed thereto. The controls can be configured to detect a wide variety of hand, wrist, and finger movements by the surgeon 230A to allow the surgeon to intuitively perform a procedure on the patient 225 using one or more medical tools installed to the manipulator arms 235A-235D.

The auxiliary system 215 can include one or more computing devices configured to perform processing operations within the surgical system 200. For example, the one or more computing devices can control and/or coordinate operations performed by various other components (e.g., the robotic medical system 205, the user control system 210) of the surgical system 200. A computing device included in the user control system 210 can transmit instructions to the robotic medical system 205 by way of the one or more computing devices of the auxiliary system 215. The auxiliary system 215 can receive and process image data representative of imagery captured by one or more imaging devices (e.g., medical tools) attached to the robotic medical system 205, as well as other data stream sources received from the visualization tool. For example, one or more image capture devices (e.g., the image capture devices 104) can be located within the surgical system 200. These image capture devices can capture images from various viewpoints within the surgical system 200. These images (e.g., video streams) can be transmitted to the visualization tool 220, which can then passthrough those images to the auxiliary system 215 as a single combined data stream. The auxiliary system 215 can then transmit the single video stream (including any data stream received from the medical tool(s) of the robotic medical system 205) to present on a display (e.g., the display 112) of the user control system 210.

In some embodiments, the auxiliary system 215 can be configured to present visual content (e.g., the single combined data stream) to other team members (e.g., the medical personnel 230B-230D) who may not have access to the user control system 210. Thus, the auxiliary system 215 can include a display 240 configured to display one or more user interfaces, such as images of the surgical site, information associated with the patient 225 and/or the surgical procedure, and/or any other visual content (e.g., the single combined data stream). In some embodiments, display 240 can be a touchscreen display and/or include other features to allow the medical personnel 230A-230D to interact with the auxiliary system 215.

The robotic medical system 205, the user control system 210, and the auxiliary system 215 can be communicatively coupled one to another in any suitable manner. For example, in some embodiments, the robotic medical system 205, the user control system 210, and the auxiliary system 215 can be communicatively coupled by way of control lines 245, which can represent any wired or wireless communication link as can serve a particular implementation. Thus, the robotic medical system 205, the user control system 210, and the auxiliary system 215 can each include one or more wired or wireless communication interfaces, such as one or more local area network interfaces, Wi-Fi network interfaces, cellular interfaces, etc.

The surgical system 200 can include other or additional components or elements that can be needed or considered desirable to have for the medical session for which the surgical system is being used.

The present solution can include a system 100 that can include one or more processors 170 coupled with memory (e.g., 172). The one or more processors 170 can be configured via run instructions and/or data stored in memory 172 to implement, provide, execute or run functions, features or embodiments described herein. The one or more processors 170 can be configured to receive a plurality of input features 140 that can be associated with a prediction 124. The prediction 124 can be made via a first model (e.g., medical procedure model 122) trained with machine learning, such as based on, or using, a plurality of video streams 162 of various procedures (e.g., surgeries, or other medical treatments). The prediction 124 can be for a video stream 162 that captures a procedure performed with a robotic medical system 110. For example, the medical procedure model 122 can receive a videos stream 162 of a medical procedure (e.g., surgery or a treatment) and provide a prediction 124 using, relying on, based on, or corresponding to input features 140, such as model performances 142, model confidence scores 144, metadata 146, identified features 148, model metrics 150, workflow data 152, tasks data 154 and event data 156. The prediction 124 can correspond to the entire video stream 162 or a portion of video stream 162.

Prediction 124 can correspond to a task, an action, a phase of a procedure, an order of tasks, a success or failure of with respect to a task, a portion of a procedure or the whole procedure or any determination, insight or inference on any portion of the video stream 162. Prediction 124 can include a description of procedure tasks, commentary on the workflow of the procedure, description of actions taken by a surgeon in the video stream 162, identification of medical tools 108 used in a surgery or any other action or task corresponding to the video stream 162.

The one or more processors 170 can be configured to determine, via a second model (e.g., confidence model 126) trained with machine learning, a level of confidence 128 in the prediction 124 made via the first model (e.g., medical procedure model 122). The level of confidence 128 can be determined based on the input features 140 input into the confidence model 126. For example, any combination of model performances 142, model confidence scores 144, metadata 146, identified features 148, model metrics 150, workflow data 152, tasks data 154 and event data 156 can be input into the confidence model 126 to provide a confidence level 128 for the given prediction 124.

The one or more processors 170 can attribute the level of confidence 128 among at least two input features 140 of the plurality of input features 140. For example, the one or more processors 170 can utilize a sensitivity function 130 to determine a portion of, or confidence attribution 132 of the confidence level 128 to any of the input features 140, including model performances 142, model confidence scores 144, metadata 146, identified features 148, model metrics 150, workflow data 152, tasks data 154 and event data 156. Sensitivity function 130 can determine confidence attribution 132 to any one or more of the input features 140, such as two input features 140, three input features 140 or more.

The one or more processors 170 can provide, for display via a display device 112, an indication 164 overlaid on the video stream 162 of the confidence attribution 132 of the level of confidence 128 among the at least two input features 140. For example, the one or more processors 170 can provide to a display 112 indications 164 providing insights, explanation or determinations corresponding to predictions 124. Indications 164 can provide confidence levels 128 and confidence attributions with respect to various input features 140. The indications 164 can be overlaid and displayed along with the video stream 162 and/or video files 166 on the display 112.

The one or more processors 170 can be configured to identify one or more portions of the video stream corresponding to the confidence level being below a threshold.

For instance, the confidence model 126 can determine that the predictions 124 for one or more portions of the video stream 162 have confidence levels 128 that are below a confidence threshold, which can be up to 95%, 90%, 85%, 80%, 75%, 70%, 65% 60% or below 60% for a given portion of the video stream 162. The one or more processors 170 can be configured to generate a video file 166 comprising the one or more portions of the video stream 162 having the confidence level below the threshold. For instance, the data stream processor 160 can compile, combine or arrange the portions of the video stream for which the confidence levels are below the threshold into a video file. The video file 166 can then be presented to the user (e.g., surgeon or other medical professional involved with the procedure captured in the video stream) to provide explanations, comments or insights for the given one or more portions in the video stream 162 (e.g., compiled in the video file 166).

The one or more processors 170 can be configured to provide a prompt for a user to input information (e.g., 118) on one or more portions of a video file 166 comprising one or more portions of the video stream 162 having the confidence level 128 below a threshold. For instance, a user interface 116 on a user device 114 (e.g., a computer station) can provide a prompt for the user (e.g., a surgeon) to provide user inputs (e.g., comments, explanations, insights or other descriptions) for the one or more portions of the video stream 162. The one or more processors 170 can be configured to receive the information from the user. For instance, the data processing system 120 can receive the user inputs 118 received via the user interface 116 and have the data stream processor 160 compile, include or overlay the user inputs into the video files 166 or the one or more portions of the video stream 162.

The one or more processors 170 can be configured to determine, via the second model (e.g., confidence model 126), a first portion (e.g., 132) of the level of confidence 128 to attribute to a first input feature 140 of the at least two input features 140. For instance, the first input feature of the two input features 140 can be attributed a first confidence attribution 132. The first confidence attribution 132 can be from 0.1% to 99.9%, and can be indicative of the percentage amount which the first input feature 140 contributed to the confidence level 126. The one or more processors 170 can be configured to determine, via the second model (e.g., confidence model 126), a second portion (e.g., 132) of the level of confidence 126 to attribute to a second input feature 140 of the least two input features 140. The second input feature 140 can be attributed to a second confidence attribution 132, which can correspond to the remaining percentage (e.g., up to 0.1% to 99.9% that is left over from the attribution of the first input feature). For instance, the two input features 140 can include for example, confidence attributions 132 of 80% and 20%, 70% and 25% (e.g., other input features attributing to the remaining 5%), 90% and 10% or any other apportionment 132, respectively.

The one or more processors 170 can be configured to determine, via the first model (e.g., medical procedure model 122) trained using a plurality of video streams (e.g., streams, such as the video stream 162) corresponding to a plurality of medical procedures, the plurality of input features 140. The first model (e.g., medical procedure model 122) can output the input features 140, such as model performances 142, model confidence scores 144, metadata 146, identified features 148, model metrics 150, workflow data 152, tasks data 154 and event data 156. The one or more processors 170 can be configured to determine, via the second model (e.g., confidence model 126), the level of confidence 128 according to the plurality of input features 140 input into the second model 126. For example, the confidence model 126 can determine the level of confidence 128 based on, according to, or responsive to any of the plurality of input features 140 considered, processed or used as input in the second model (e.g., 126).

The plurality of input features 140 can include two or more of: a known model performance 142 corresponding to the procedure, a model confidence score 144 of the prediction, a metadata 146 of the video stream, a feature identified 148 from the video stream 162, a metric (e.g., 150) of one or more modeled procedures corresponding to the procedure, a workflow (e.g., 152) of the procedure and a plurality of tasks (e.g., 154) of the workflow 152. The one or more processors 170 can be configured to determine, via the second model (e.g., 126), that the attribution (e.g., 132) of the level of confidence 128 corresponding to a first input feature 140 of the two input features 140 exceeds a threshold. The one or more processors 170 can be configured to provide, for display via the display device 112, the indication responsive to the attribution 132 of the level of confidence 128 corresponding to the first input feature 140 exceeding the threshold.

The first input feature of the at least two input features include one of: a workflow (e.g., 152) of the procedure, a plurality of tasks (e.g., 154) of the workflow 152 or a tool feature (e.g., identified feature 148 corresponding to medical tool 108) used by a medical professional during the procedure. The one or more processors 170 can be configured to detect, via the second model, that the first input feature during a first portion of the video stream differs from a corresponding first input feature of a modeled procedure. The one or more processors 170 can be configured to provide, for display, the indication 164 corresponding to the first input feature 140 overlaid during the first portion of the video stream 162. The one or more processors 170 can be configured to receive, via a user interface 116, an input (e.g., 118) from a user corresponding to a portion of the video stream 162 affecting the portion (e.g., 132) of level of confidence 128 to the first input feature 140. The one or more processors 170 can be configured to provide, for display via the display device 112, a second indication 164 comprising the input overlaid during the portion of the video stream 162.

In some aspects the present solution can relate to a non-transitory computer readable medium storing program instructions for causing at least one processor 170 to receive a plurality of input features 140 associated with a prediction 124, made via a first model trained (e.g., medical procedure model 122) with machine learning, for a video stream 162 that captures a procedure performed with a robotic medical system 110. The program instructions can cause the at least one processor 170 to determine, via a second model (e.g., confidence model 126) trained with machine learning, a level of confidence 128 in the prediction 124 made via the first model. The program instructions can cause the at least one processor 170 to attribute (e.g., 132) the level of confidence 126 among at least two input features 140 of the plurality of input features 140. The program instructions can cause the at least one processor 170 to provide, for display via a display device 112, an indication 164 overlaid on the video stream 162 of the attribution (e.g., 132) of the level of confidence 128 among the at least two input features 140.

The program instructions can cause the at least one processor 170 to attribute (e.g., 132) the level of confidence 128 among at least the first input feature 140 and a second input feature 140 of the plurality of input features 140. The program instructions cause the at least one processor 170 to provide, for display via a display device 112, the indication 164 overlaid on the video stream 162 of the attribution 132 of the level of confidence 128 among the first input feature 140 and the second input feature 140.

Figure 3:
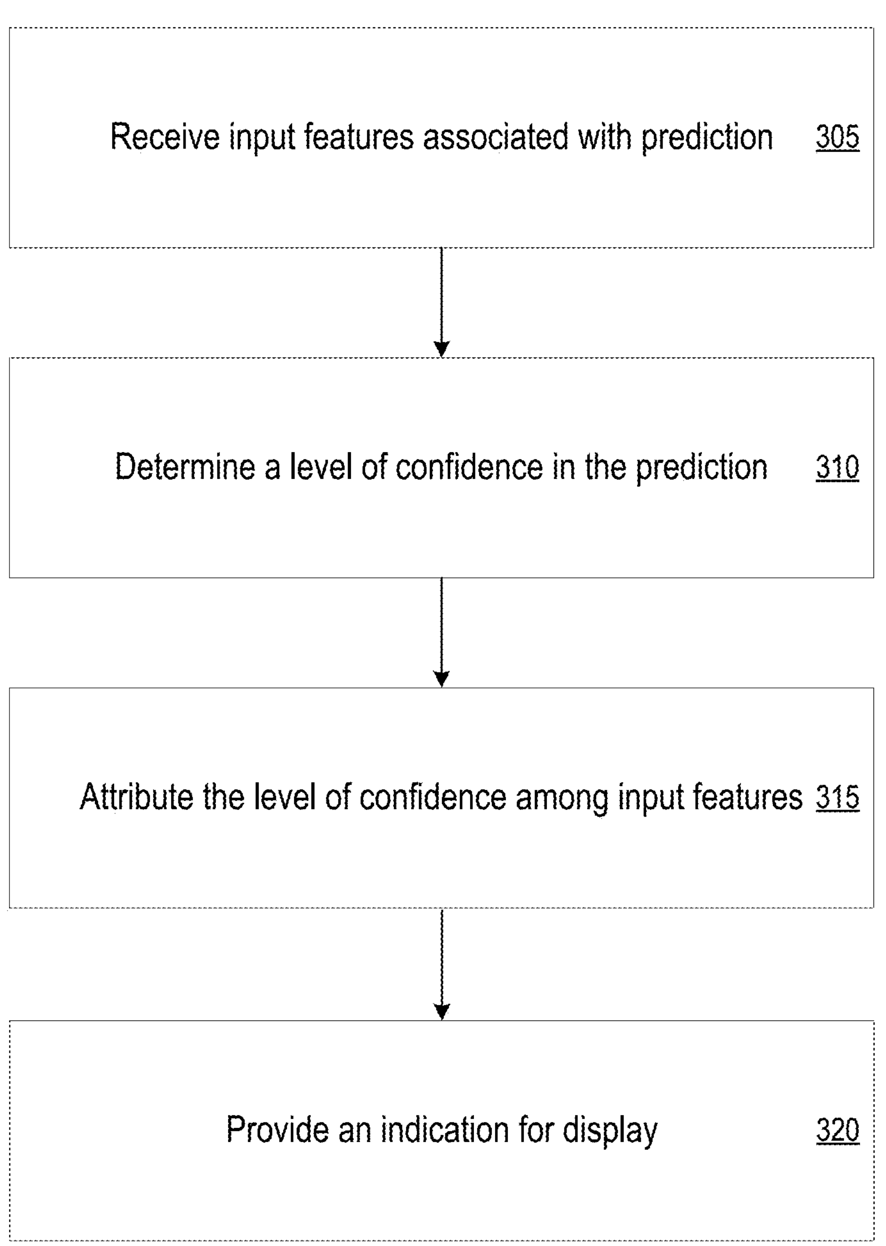
FIG. 3 illustrates an example flowchart of an ML-based medical procedure analysis with interpretable model confidence rankings.

FIG. 3 depicts an example flowchart of a process or a method 300 an ML-based medical procedure analysis with interpretable model confidence rankings. The process 300 can be performed by a system 100 having one or more processors 170 executing computer-readable instructions stored on a memory 172. The process 300 can be performed by the data stream processor 160, and particularly using instructions or data stored on non-transitory computer-readable memory (e.g., the memory 172). The process or method 300 can include acts 305 through 320. At 305, the method can include receiving input features associated with a prediction. At 310, the method can include determining a level of confidence in the prediction. At 315, the method can include attributing the level of confidence among input features. At 320, the method can include providing an indication for display.

At 305, the method can receive input features associated with a prediction. For example, the method can include one or more processors coupled with memory (e.g., processors of a data processing system) receiving a plurality of input features associated with a prediction. The method can include the data processing system receiving from a medical procedure model the plurality of input features. The plurality of input features can be input features generated, provided, processed or determined or made via a first model (e.g., medical procedure model) that can be trained with machine learning. The received plurality of input features associated with the prediction can be for a video stream that captures a procedure performed with a robotic medical system. The procedure can include a medical procedure, such as a surgery, or any other medical treatment.

The one or more processors (e.g., of the data processing system) can determine the plurality of input features via the first model (e.g., medical procedure model) that can be trained using a plurality of video streams corresponding to a plurality of medical procedures. The plurality of input features can include one, two or more of: a known model performance corresponding to the procedure, a model confidence score of the prediction, a metadata of the video stream, a feature identified from the video stream, a metric of one or more modeled procedures corresponding to the procedure, a workflow of the procedure and a plurality of tasks of the workflow.

Prediction can include a determination or prediction of occurrence of a task, an action, or phase of a procedure. Prediction can include an order of tasks or a chain of tasks (e.g., workflow). Prediction can include a success or failure of with respect to a task, or with respect to a portion of a procedure or the whole procedure or any determination, insight or inference on any portion of the video stream. Prediction can include a description of procedure tasks, commentary on the workflow of the procedure, description of actions taken by a medical professional (e.g., a surgeon) captured or recorded in the video stream, identification of medical tools used in a medical procedure (e.g., surgery tools) or any other action or task corresponding to actions or occurrences in the video stream.

A first input feature of the at least two input features can include one of: a workflow of the procedure, a plurality of tasks of the workflow or a tool feature used by a medical professional during the procedure. The one or more processors can detect, via the second model (e.g., confidence model), that the first input feature during a first portion of the video stream differs from a corresponding first input feature of a modeled procedure. For example, the confidence model can include can recognize or identify an input feature in a portion of a video stream and can determine that the identified input feature differs from a modeled input feature expected based on the model procedure. The confidence model can determine, adjust or modify the confidence level based on such a determination.

At 310, the method can include determining a level of confidence in the prediction. For example, the one or more processors can determine, via a second model (e.g., confidence model) that can be trained with machine learning, a level of confidence in the prediction made via the first model. For example, the confidence model can determine a level of confidence for a particular prediction. The level of confidence can be confidence that is greater than 99%, confidence that is greater than 95%, 90%, 85%, 80%, 75%, 70%, 65%, 60%, 55% or 50%. The level of confidence can vary based on input features 140 corresponding to the procedure captured in the video stream agreeing, matching or conforming to expected modeled input features.

For example, the level of confidence can be determined, generated, adjusted, increased or decreased based on a known model performance corresponding to the procedure matching or not matching that of the modeled procedure within a predetermined threshold or tolerance range. The level of confidence can be determined, generated, adjusted, increased or decreased based on model confidence score of the prediction matching or not matching that of the modeled procedure within a predetermined threshold or tolerance range.

For example, the level of confidence can be determined, generated, adjusted, increased or decreased based on metadata of the video stream matching or not matching that of modeled procedure within a predetermined threshold or tolerance range. For example, metadata can indicate that the recorded procedure is from a facility (e.g., hospital) that is new to the data of the data processing system and therefore the confidence level can be lower.

The level of confidence can be determined, generated, adjusted, increased or decreased based on a feature identified from the video stream matching or not matching that of the modeled procedure within a predetermined threshold or tolerance range. For example, the captured procedure can include a surgeon using a different tool at a particular predicted phase of the surgery than a modeled tool in a modeled surgery of the same type.

The level of confidence can be determined, generated, adjusted, increased or decreased based on a metric of one or more modeled procedures corresponding to the procedure matching or not matching that of the captured procedure within a predetermined threshold or tolerance range. The level of confidence can be determined, generated, adjusted, increased or decreased based on a workflow of the procedure matching or not matching that of the workflow of a modeled procedure within a predetermined threshold or tolerance range. For instance, the order of tasks or actions in the captured procedure can differ from that of the modeled procedure.

The level of confidence can be determined, generated, adjusted, increased or decreased based on a plurality of tasks of the workflow of the procedure captured by the video stream matching or not matching that of the modeled procedure within a predetermined threshold or tolerance range. For example, the modeled procedure can have one or more tasks or actions that do not match with the captured procedure. In response, the confidence model can adjust (e.g., decrease) the confidence level in the prediction.

The one or more processors can identify one or more portions of the video stream corresponding to the confidence level is below a threshold. The one or more processors can generate a video file comprising the one or more portions of the video stream having the confidence level below the threshold and determine, via the second model, the level of confidence according to the plurality of input features input into the second model. For example, the data processing system can generate a video file compiling any number of portions of the video stream (e.g., video stream portions of specific tasks or actions in the procedure) for which the confidence levels for the predictions made are below a threshold, such as a threshold of 95%, 90%, 85%, 80%, 75%, 70%, 65%, 60% or below.

At 315, the method can include attributing the level of confidence among input features. The one or more processors can attribute the level of confidence among at least two input features of the plurality of input features. For example, the sensitivity function can provide confidence attributions for any two input features of: a known model performance corresponding to the procedure, a model confidence score of the prediction, a metadata of the video stream, a feature identified from the video stream, a metric of one or more modeled procedures corresponding to the procedure, a workflow of the procedure and a plurality of tasks of the workflow. The confidence attribution can be made in accordance with percentages adding up to a 100% for all of the input features involved. For example, a first input feature can be apportioned 70%, while a second input feature can be apportioned 30% of the confidence contribution. For example, a first input feature can be apportioned 60%, while a second input feature can be apportioned 20%, leaving 20% of the apportionment to other input features affecting the confidence level.

The one or more processors can determine, via the second model (e.g., sensitivity function of a confidence model), a first portion of the level of confidence to attribute to a first input feature of the at least two input features. The one or more processors can determine, via the second model (e.g., sensitivity function of a confidence model), a second portion of the level of confidence to attribute to a second input feature of the least two input features. The one or more processors can determine, via the second model, that the attribution of the level of confidence corresponding to a first input feature of the two input features exceeds a threshold. For example, one of the input features can be apportioned a confidence attribution of 62%, whereas threshold is 60%. In response to exceeding the threshold, the data processing system can generate an indication to include in the overlay of the video stream or a video file to be generated.

At 320, the method can include providing an indication for display. The one or more processors can provide, for display via a display device, an indication overlaid on the video stream of the attribution of the level of confidence among the at least two input features. The indication can include text describing, providing or indicating the prediction and the confidence levels. The indication can include confidence attributions to the input features that contributed to the confidence level the most. For example, two input features can be determined by the sensitivity function to be most sensitive and affect the confidence level more than other input features of the plurality of input features. Indications included in the video stream (e.g., overlaid over the video stream, subtitled in the video stream, or voiced over the video stream) can indicate the confidence attributions, confidence levels and predictions throughout various tasks, phases and actions of the procedure in the video stream or video file.

The one or more processors can provide a prompt for a user (e.g., a medical professional, such as a surgeon) to input information (e.g., comments or text) on one or more portions of a video file comprising one or more portions of the video stream having the confidence level below a threshold. For example a user interface can allow a surgeon to provide user inputs to comment on various aspects of the vides stream or video files for which confidence levels are below a threshold level (e.g., 80%) or above a threshold level (e.g., above 99%).

The one or more processors can receive the information from the user (e.g., via a user input in the user interface), and provide, for display via the display device, the indication. The indication can be provided responsive to the attribution of the level of confidence corresponding to the first input feature exceeding the threshold.

The one or more processors can provide, for display, the indication corresponding to the first input feature overlaid during the first portion of the video stream. The one or more processors can receive, via a user interface, an input from a user (e.g., a surgeon) corresponding to a portion of the video stream affecting at least a portion of the level of confidence to the first input feature or the portion of the level of confidence associated with the first input feature. The one or more processors can provide, for display via the display device, a second indication comprising the input overlaid during the portion of the video stream. The second indication can include the input from the user (e.g., surgeon) explaining anomalies, deficiencies, unusual circumstances or reasons for changes in the expected procedure. For example, the models can detect a suturing motion in a task or a phase of surgery in which the model does not expect any suturing to occur. This can cause the particular prediction to be given a low or reduced confidence level.

Figure 4:
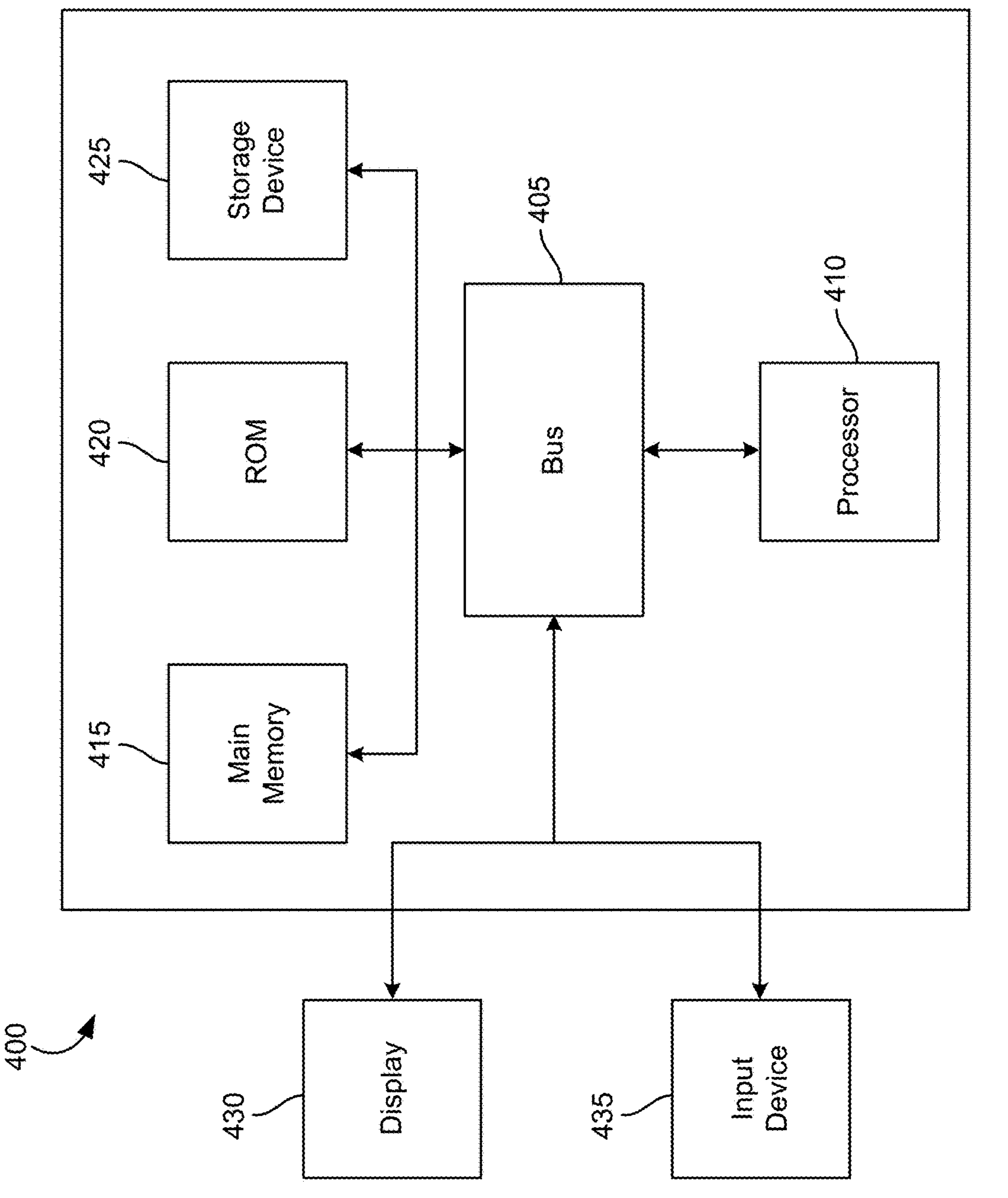
FIG. 4 illustrates an example computer system that can be used for performing the embodiments of the present solution.

Turning to FIG. 4, an example block diagram of an example computer system 400 is shown, in accordance with some embodiments. The computer system 400 can be any computing device used herein and can include or be used to implement a data processing system or its components. The computer system 400 includes at least one bus 405 or other communication component or interface for communicating information between various elements of the computer system. The computer system further includes at least one processor 410 or processing circuit coupled to the bus 405 for processing information. The computer system 400 also includes at least one main memory 415, such as a random-access memory (RAM) or other dynamic storage device, coupled to the bus 405 for storing information, and instructions to be executed by the processor 410. The main memory 415 can be used for storing information during execution of instructions by the processor 410. The computer system 400 can further include at least one read only memory (ROM) 420 or other static storage device coupled to the bus 405 for storing static information and instructions for the processor 410. A storage device 425, such as a solid-state device, magnetic disk or optical disk, can be coupled to the bus 405 to persistently store information and instructions.

The computer system 400 can be coupled via the bus 405 to a display 430, such as a liquid crystal display, or active-matrix display, for displaying information. An input device 435, such as a keyboard or voice interface can be coupled to the bus 405 for communicating information and commands to the processor 410. The input device 435 can include a touch screen display (e.g., the display 430). The input device

435 can also include a cursor control, such as a mouse, a trackball, or cursor direction keys, for communicating direction information and command selections to the processor 410 and for controlling cursor movement on the display 430.

The processes, systems and methods described herein can be implemented by the computer system 400 in response to the processor 410 executing an arrangement of instructions contained in the main memory 415. Such instructions can be read into the main memory 415 from another computer-readable medium, such as the storage device 425. Execution of the arrangement of instructions contained in the main memory 415 causes the computer system 400 to perform the illustrative processes described herein. One or more processors in a multi-processing arrangement can also be employed to execute the instructions contained in the main memory 415. Hard-wired circuitry can be used in place of or in combination with software instructions together with the systems and methods described herein. Systems and methods described herein are not limited to any specific combination of hardware circuitry and software.

Although an example computing system has been described in FIG. 4, the subject matter including the operations described in this specification can be implemented in other types of digital electronic circuitry, or in computer software, firmware, or hardware, including the structures disclosed in this specification and their structural equivalents, or in combinations of one or more of them.

Figure 5:
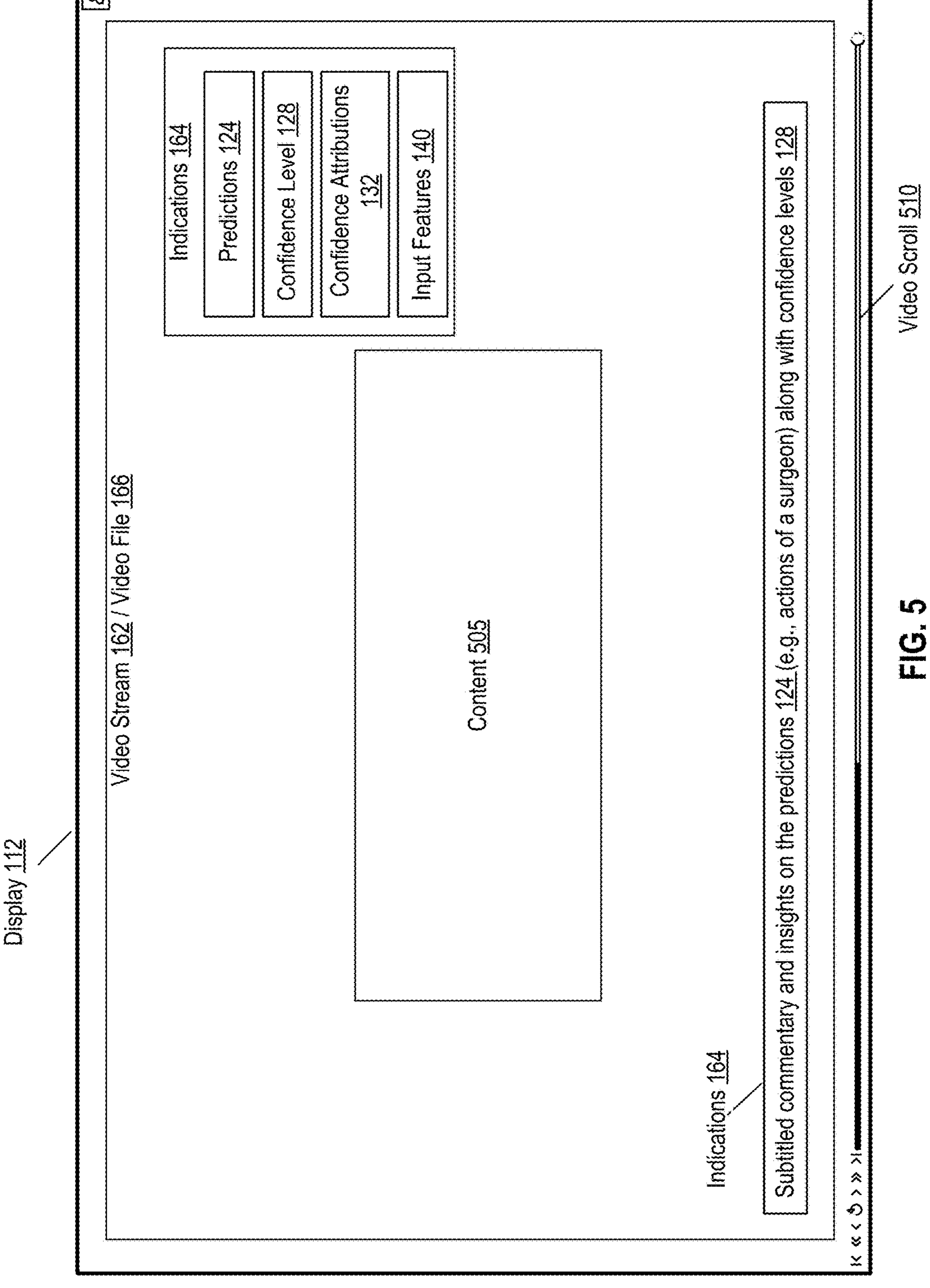
FIG. 5 illustrates an example display of a video stream or video files, in accordance with the embodiments of the present solution.

FIG. 5 provides an example 500 of a display 112 that presents a video stream 162 or video files 166, in accordance with the embodiments of the present solution. Example 500 illustrates a display 112 playing a content 505 in a video stream 162 or video file 166. Content 505 can include any video and/or audio recording of a medical procedure (e.g., a surgery). Display 112 can also present a video scroll 510, which can include a timeline bar allowing a user to scroll backwards and forwards through the video. Overlaid over the content 505 in the video stream 162 or video files 166 are indications 164. Indications 164 can include, indicate, discuss, present or state predictions 124 and their corresponding confidence levels 128. Indications 164 can include, indicate, discuss, present or state confidence attributions 132 for each input feature 140.

Indications 164 can be visual (e.g., text or color coded signals) or audio-based (e.g., stated in the video). Any portion of indications 164 can be stated using different colors, fonts or symbols. For example, a high confidence levels 128 (e.g., over 99%) can be indicated by a green light or lamp indication 164 overlaid over a portion of the content 505, while a low confidence level 128 (e.g., below 80%) can be indicated using a red light or lamp indication 164, and a medium confidence level 128 (e.g., between 99% and 80%) can be indicated using a yellow light or lamp indication 164.

The high, low and medium levels of confidence 128 can be determined using normalization functions. For example, each prediction 124 can have its own confidence level 128 and the solution can rank the predictions 124 based on the confidence levels 128 (highest to lowest), identifying the lowest third of the scores as the low levels of confidence 128, the mid-range third of the scores as middle confidence level 128 and highest third as high confidence levels 128.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods can be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A system comprising:

one or more processors, coupled with memory, to:

receive a plurality of input features associated with a prediction, made via a first model trained with machine learning, for a video stream that captures a procedure performed with a robotic medical system;

determine, via a second model that is different from the first model, a level of confidence in the prediction made via the first model;

attribute, via the second model, portions of the level of confidence among at least two input features of the plurality of input features;

modify the video stream to include an indication overlaid on the video stream, the indication corresponding to the confidence level attributed to the at least two input features; and provide, for display via a display device, the modified video stream including the indication overlaid on the video stream.

2. The system of claim 1, comprising the one or more processors to:

identify one or more portions of the video stream corresponding to the level of confidence below a threshold; and generate a video file comprising the one or more portions of the video stream having the level of confidence below the threshold.

3. The system of claim 1, comprising the one or more processors to:

provide a prompt for a user to input information on one or more portions of a video file comprising one or more portions of the video stream having the level of confidence below a threshold; and receive the information from the user.

4. The system of claim 1, comprising the one or more processors to:

determine, via the second model using a sensitivity function, a first portion of the level of confidence to attribute to a first input feature of the at least two input features; and determine, via the second model using the sensitivity function, a second portion of the level of confidence to attribute to a second input feature of the at least two input features.

5. The system of claim 1, comprising the one or more processors to:

determine, via the first model trained using a plurality of video streams corresponding to a plurality of medical procedures, the plurality of input features; and determine, via the second model, the level of confidence according to the plurality of input features input into the second model.

6. The system of claim 1, wherein the plurality of input features includes two or more of: a known model performance corresponding to the procedure, a model confidence score of the prediction, a metadata of the video stream, a feature identified from the video stream, a metric of one or more modeled procedures corresponding to the procedure, a workflow of the procedure and a plurality of tasks of the workflow.

7. The system of claim 1, comprising the one or more processors to:

determine, via the second model, that the attribution of the level of confidence corresponding to a first input feature of the at least two input features exceeds a threshold; and provide, for display via the display device, the indication responsive to the attribution of the level of confidence corresponding to the first input feature exceeding the threshold.

8. The system of claim 1, wherein a first input feature of the at least two input features includes one of: a workflow of the procedure, a plurality of tasks of the workflow or a tool feature used by a medical professional during the procedure, the system comprising the one or more processors to:

detect, via the second model, that the first input feature during a first portion of the video stream differs from a corresponding first input feature of a modeled procedure; and provide, for display, the indication corresponding to the first input feature overlaid during the first portion of the video stream.

9. The system of claim 1, comprising the one or more processors to:

receive, via a user interface, an input from a user corresponding to a portion of the video stream affecting the portion of the level of confidence associated with the first input feature; and provide, for display via the display device, a second indication comprising the input overlaid during the portion of the video stream.

10. A method comprising:

receiving, by one or more processors coupled with memory, a plurality of input features associated with a prediction, made via a first model trained with machine learning, for a video stream that captures a procedure performed with a robotic medical system;

determining, by the one or more processors via a second model that is different from the first model, a level of confidence in the prediction made via the first model;

attributing, by the one or more processors via the second model, portions of the level of confidence among at least two input features of the plurality of input features;

modifying, by the one or more processors, the video stream to include an indication overlaid on the video stream, the indication corresponding to the confidence level attributed to the at least two input features; and providing, by the one or more processors, for display via a display device, the modified video stream including the indication overlaid on the video stream.

11. The method of claim 10, comprising:

identifying, by the one or more processors, one or more portions of the video stream corresponding to the level of confidence below a threshold; and generating, by the one or more processors, a video file comprising the one or more portions of the video stream having the level of confidence below the threshold.

12. The method of claim 10, comprising:

providing, by the one or more processors, a prompt for a user to input information on one or more portions of a video file comprising one or more portions of the video stream having the level of confidence below a threshold; and receiving, by the one or more processors, the information from the user.

13. The method of claim 10, comprising:

determining, by the one or more processors via the second model, using a sensitivity function, a first portion of the level of confidence to attribute to a first input feature of the at least two input features; and determining, by the one or more processors via the second model, using a sensitivity function, a second portion of the level of confidence to attribute to a second input feature of the at least two input features.

14. The method of claim 10, comprising:

determining, by the one or more processors via the first model trained using a plurality of video streams corresponding to a plurality of medical procedures, the plurality of input features; and determining, by the one or more processors via the second model, the level of confidence according to the plurality of input features input into the second model.

15. The method of claim 10, wherein the plurality of input features includes two or more of: a known model performance corresponding to the procedure, a model confidence score of the prediction, a metadata of the video stream, a feature identified from the video stream, a metric of one or more modeled procedures corresponding to the procedure, a workflow of the procedure and a plurality of tasks of the workflow.

16. The method of claim 10, comprising:

determining, by the one or more processors via the second model, that the attribution of the level of confidence corresponding to a first input feature of the at least two input features exceeds a threshold; and providing, by the one or more processors for display via the display device, the indication responsive to the attribution of the level of confidence corresponding to the first input feature exceeding the threshold.

17. The method of claim 10, wherein a first input feature of the at least two input features includes one of: a workflow of the procedure, a plurality of tasks of the workflow or a tool feature used by a medical professional during the procedure, comprising:

detecting, by the one or more processors via the second model, that the first input feature during a first portion of the video stream differs from a corresponding first input feature of a modeled procedure; and providing, by the one or more processors for display, the indication corresponding to the first input feature overlaid during the first portion of the video stream.

18. The method of claim 10, comprising:

receiving, by the one or more processors via a user interface, an input from a user corresponding to a portion of the video stream affecting the portion of the level of confidence associated with the first input feature; and providing, by the one or more processors for display via the display device, a second indication comprising the input overlaid during the portion of the video stream.

19. A non-transitory computer readable medium storing program instructions for causing at least one processor to:

receive a plurality of input features associated with a prediction, made via a first model trained with machine learning, for a video stream that captures a procedure performed with a robotic medical system;

determine, via a second model that is different from the first model, a level of confidence in the prediction made via the first model;

attribute, via the second model, portions of the level of confidence among at least two input features of the plurality of input features;

modify the video stream to include an indication overlaid on the video stream, the indication corresponding to the confidence level attributed to the at least two input features; and provide, for display via a display device, the modified video stream including the indication overlaid on the video stream.

20. The non-transitory computer readable medium of claim 19, wherein the program instructions cause the at least one processor to:

attribute the level of confidence among at least a first input feature and a second input feature of the plurality of input features; and provide, for display via the display device, the indication overlaid on the video stream of the attribution of the level of confidence among the first input feature and the second input feature.

* * * * *